United States Patent
Allen

(10) Patent No.: US 6,608,109 B2
(45) Date of Patent: *Aug. 19, 2003

(54) COMPOSITION COMPRISING L-ARGININE AS A MUSCLE GROWTH STIMULANT AND USE THEREOF

(76) Inventor: Ann de Wees Allen, 8300 Boone Blvd., Suite 500, Vienna, VA (US) 22182

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/938,801

(22) Filed: Sep. 26, 1997

(65) Prior Publication Data

US 2003/0119888 A1 Jun. 26, 2003

Related U.S. Application Data

(63) Continuation of application No. 08/784,132, filed on Jan. 15, 1997, now abandoned, which is a continuation of application No. 08/562,395, filed on Nov. 24, 1995, now abandoned, which is a continuation of application No. 08/215,667, filed on Mar. 22, 1994, now abandoned, which is a continuation of application No. 07/793,837, filed on Nov. 20, 1991, now abandoned.

(51) Int. Cl.[7] .................. A61K 31/95; A61K 31/19; A61K 31/135
(52) U.S. Cl. .................. 514/561; 514/563; 514/564; 514/565; 514/570; 514/574; 514/658
(58) Field of Search ................ 514/574, 561, 514/563, 570, 564, 658, 565

(56) References Cited

U.S. PATENT DOCUMENTS 4,604,286 A * 8/1986 Kawajiri .................... 514/561
4,734,401 A * 3/1988 Blouin ........................ 514/2
5,026,721 A * 6/1991 Dudrick et al. ............. 514/561
5,087,624 A * 2/1992 Boynton et al. ............ 514/188

FOREIGN PATENT DOCUMENTS

AU 4068972 * 10/1973
FR 2547501 * 12/1984

OTHER PUBLICATIONS

Martindale, The Extra Pharmacopoeia, 28th edition (1982) p. 49.*

Salomon, Franco et al "The Effects of Treatment with . . . " Growth Hormone Treatment in Adults, vol. 321 No. 26, pp, 1797–1803 (Publication date unknown).

Vance, "Growth Hormone for the Elderly" The New England Jour. of Medicine, vol. 321, No. 1, Jul. 5, 1990, pp. 52–54.

Rudman, et al "Growth Hormone Treatment of Frailty in Men over 60" New England Jour. of Medicine Jul. 5, 1990, pp. 1–9.

Colgan, "Fitness and Aging", Muscular Development, pp. 138–140. Publication date unknown.

Colgan, "Fitness and Aging" Muscular Development, pp. 126–128. Publication date unknown.

* cited by examiner

Primary Examiner—Raymond Henley, III
(74) Attorney, Agent, or Firm—Saliwanchik, Lloyd & Saliwanchik

(57) ABSTRACT

A composition for stimulating muscle growth, comprising an effective amount of L-arginine or a salt thereof, a pH control agent for controlling the pH at less than 7 and a pharmaceutically acceptable carrier. A method of using the composition to achieve muscle growth or an immune response is also described.

15 Claims, No Drawings

COMPOSITION COMPRISING L-ARGININE AS A MUSCLE GROWTH STIMULANT AND USE THEREOF

This is a continuation of application Ser. No. 08/784,132, filed Jan. 15, 1997, now abandoned, which is a continuation of application Ser. No. 08/562,395, filed Nov. 24, 1995, now abandoned, which is a continuation of application Ser. No. 08/215,667, filed Mar. 22, 1994, now abandoned, which is a continuation of application Ser. No. 07/793,837, filed Nov. 20, 1991, now abandoned.

BACKGROUND OF THE INVENTION

1. Field of the Invention

The present invention relates to a novel composition useful as a replacement for steroids as a muscle growth stimulant and for stimulating an immune response, and to the use thereof.

2. Description of the Prior Art

The problems of maintaining muscle mass while minimizing the accumulation of fat has long been an issue of concern to athletes. While exercise is one of the main mechanisms for achieving that goal, food and/or vitamin supplements, as well as pituitary growth hormone, are necessary for muscle growth. Such ergogenic aids, that is supplements which stimulate muscle growth, include the three amino acids, leucine, isoleucine and valine. Human Growth Hormone (HGH) has also been considered. Zale, N., "Amino Acids—Growth Hormone Stimulants Fact or Fiction?", *Iron Man Magazine*, Jan. 1985 and New England Journal of Medicine (1990). Growth hormone produces an anabolic effect which includes the process of converting amino acids into protein. The cost of using human growth hormone is very high. Thus, economic reality generally detracts from its use.

Likewise, the use of steroids to improve performance and increase muscle mass is fraught with disadvantages. Anabolic steroids have undesirable side effects which are linked to a variety of serious health problems including cardiovascular disease and liver cancer.

Chemical compounds have also been found to be important not for their direct influence on muscle growth, but rather as complements to or synergists for other compounds which stimulate muscle growth. Boron is one such compound. Boron is an essential mineral which is believed to play an important role in the retention of calcium. Likewise, chromium has been found to be a beneficial supplement for athletes. It has been speculated that chromium losses are twice as high on a workout day versus a non-workout day.

In addition, trans-ferulic acid, which is the metabolically active form of gamma oryzanol, is believed to increase the production of key brain chemicals thereby causing increased secretion of growth hormone.

In spite of the extensive studies and research to date, there remains a long-felt need in the art for a safe and effective method of stimulating muscle growth and taking the place of steroids, especially for athletes.

SUMMARY OF THE INVENTION

Surprisingly, the present inventor has now found that the laevorotatory form of arginine (L-arginine) is useful as a muscle stimulant in a mammalian organism, especially a human, when preferably present in a formulation which contains the proper adjuvants and/or synergists. More particularly, it has been found that therapeutic doages of L-arginine, typically up to 15 g per day, can be rendered more palatable to a patient (L-arginine has an extremely unpleasant taste) and are better physiologically tolerated by a patient (reduced incidence of diarrhea, headache, flatulence, and depletion of vitamins and electrolytes) by careful control of the pH of the formulation so as to be less than 7, i.e. an acid pH. As a result, long term therapy.with L-arginine with reduced side-effects is obtained, in particular reduced depletion of acetyl choline from the brain and consequential reduced.incidence of memory loss.

In one aspect, the present invention provides a composition comprising L-arginine in a form which is palatable to a patient, physiologically tolerated and suitable for enhancing muscle growth, body fat reduction and stimulation of growth hormone in a mammalian organism, in association with a pH control agent for controling the pH of the composition at less than 7, preferably less than 6.0, for example about 3.5 to 5.5, especially 4.5 to 4.7, and an pharmaceutically acceptable carrier.

More particularly, the present invention provides a composition or complex comprising L-arginine, L-leucine, L-isoleucine, L-valine, boron (or sodium borate), vitamin B5 (calcium pantothenate), chromium, trans ferulic acid, gamma oryzanol, choline, fructose, lemon, lime and citric acid, in which the ratio of components is such that the pH of the composition is less than 7.0, preferably less than 6.0, more preferably 4.5 to 4.7. The composition suitably allows enhanced muscle growth with minimum side effects, especially over extended therapy periods, for example 4 to 8 weeks.

In another aspect, the invention provides a method for stimulating muscle growth in a mammalian organism comprising the step of administering to a host a muscle growth stimulant or enhancing effective amount of an L-arginine formulation comprising L-arginine or a salt thereof in association with a pH control agent for controlling the pH of the formulation at less than 7 and an adjuvant suitable for stimulating muscle growth.

In yet another aspect, there is provided a method of stumulating an immune response in a patient in need of such treatment, comprising the step of administering to that patient an effective amount of an L-arginine formulation in association with a suitable adjuvant and/or diluent. Preferably, the L-arginine is administered intravenously as an aqueous solution in an amount of 1–10 g per day. More preferably, the L-arginine is co-administered with an immune system stimulator which is preferably vitamin C, in an amount of 1–10 g per day.

Other objects and advantages of the present invention will be apparent from the following description.

DETAILED DESCRIPTION OF THE PREFERRED EMBODIMENTS

Arginine, 2-amino-5-guanidinovaleric acid, is a basic amino acid with a positively charged guanidinium group. The IUPAC abbreviation is Arg. Arginine can be depicted as follows.

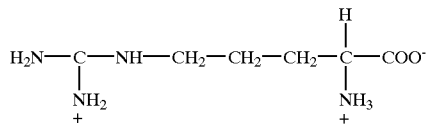

Arginine is considered to be a semi-essential amino acid. It can be synthesized in animal tissue at a rate sufficient for maintenance in the adult but not rapidly enough to support growth in the young animal. It is thus an essential amino acid for growth but not for maintenance. It is difficult to obtain therapeutic amounts in chicken and turkey, thus the food supplement of arginine.

In the mammalian body, arginine takes part in the formation of urea yielding ornithine. Arginine may be synthesized in the mammalian body from alpha-ketoglutaric acid, glutamic acid or proline.

In addition to L-arginine free base, any salt of L-arginine is suitable in the practice of the present invention. Such salts include L-arginine hydrochloride and the like. L-arginine hydrochloride is the preferred salt in the practice of the present invention.

Additional suitable anions for such a salt of L-arginine include bromide, fluoride, iodide, borate, hypobromite, hypochlorite, nitrite, nitrate, hyponitrite, sulfate, disulfate, sulfite, sulfonate, phosphate, diphosphate, phosphite, phosphonate, diphosphonate, perchlorate, perchlorite, oxalate, malonate, succinate, lactate, carbonate, bicarbonate, acetate, benzoate, citrate, tosylate, permanganate, manganate, propanolate, propanoate, ethandioate, butanoate, propoxide, chromate, dichromate, selenate, orthosilicate, metasilicate, pertechnetate, technetate, dimethanolate, dimethoxide, thiocyanate, cyanate, isocyanate, 1,4-cyclohexanedithiolate, oxidobutanoate, 3-sulfidocyclobutane-1-sulfonate, 2-(2-carboxylatoethyl)-cyclohexanecarboxylate, 2-amino-4-(methythio)-butanoate and the like. The suitable cation for most salts is hydrogen. However, other cations such as sodium, potassium and the like would be acceptable in the preparation of such a salt.

L-arginine free base is, however, preferred since it is less hydroscopic and therefore more stable. Free form amino acids are assimilated in an entirely different manner than amino acids derived from foods containing protein. The free form allows for almost immediate elevation of the level of amino acids in the blood plasma. Further, it would be essential to take the L-arginine on an empty stomach so as to minimize any competition between L-arginine and protein in the stomach.

The precise amount of L-arginine suitable for use in the practice of the present invention will vary depending on the adjuvants or synergists present, the size and kind of the mammal and the specific form, i.e., salt or base, selected.

The typical muscle growth stimulating or enhancing effective amount of L-arginine or acceptable salt thereof would be in the range of about 1.0 grams to 60 grams per day, preferably about 3.0 grams to 30 grams per day.

The L-arginine or salt thereof may be administered to a mammalian organism by any route of administration. Suitable routes would, of course, include oral, parenteral, topical, and the like. The oral dosage form is preferred in a non-tablet, non-capsule free form powder.

The present inventor has found that while L-arginine or salt thereof is useful in stimulating muscle growth, the L-arginine when taken alone on an empty stomach has some disadvantages. First, the L-arginine has an extremely unpleasant taste which makes the oral administration of large dosages difficult and sometimes impossible. Other disadvantages arising from the ingestion of L-arginine include headache, diarrhea, flatulence, depletion of electrolytes, as well as depletion of vitamins, minerals and the like. The side effects from the administration of L-arginine by itself vary significantly from individual to individual and run the gamit of mild to severe.

In order to overcome these disadvantages, the present inventor has discovered that it is possible to administer hugh dosages of L-arginine if the formulation has an acid pH, i.e. less than 7.0. The preferred pH is less than 6.0, for example 4.3 to 4.8, suitably 4.5 to 4.7. By controlling the pH in this way, it has been found that the L-arginine is more readily accepted by the gastrointestinal tract, that there is minimum depletion of normal body chemicals and is pleasant to taste. Moreover, the stability of the composition is improved as a result of ensuring that the composition has an acid pH.

The pH is preferably controlled by the presence in the L-arginine composition of a pharmaceutically acceptable acid in an amount which results in a pH of 7 or less when the composition is administered orally. A preferred acid is citric acid, but the invention is not limited to this acid and other suitable pharmaceutically acceptable acids may be employed.

The pH control agent is present in an amount so as to achieve the desired pH of less then 7. Preferably, the weight ratio of pH control agent to L-arginine in the composition is 0.001–1 pH control agent : 1 L-arginine, for example 0.5–0.9 pH control agent : 1 L-arginine. Examples of weight ranges are 0.001 mg–100 mg per 1.0 to 60 g of L-argenine, typically 2.0 to 5.0 g per 6 g of L-argenine.

A preferred formulation is set forth below:

|  | Preferred Dosage Range | Daily Preferred Dosage |
|---|---|---|
| L-Arginine (free base) | 1.0–60.0 g | 30.0 g |
| L-Leucine | 25–200 mg | 100.0 mg |
| L-Isoleucine | 25–200 mg | 50.0 mg |
| L-Valine | 25–200 mg | 50.0 mg |
| Boron (Sodium Borate) | 1.0–30 mg | 5.0 mg |
| Vitamin B5 (Calcium Pantothenate) | 10–100 mg | 50.0 mg |
| Chromium | 10–50 micrograms | 25.0 micrograms |
| Trans Ferulic Acid | 5.0–100 mg | 10 0 mg |
| Gamma Oryzanol | 5.0–100 mg | 15.0 mg |
| Choline | 10.0–700 mg | 50.0 mg |
| Fructose | 2.0–10.0 g | 6.0 g |
| Lemon (Natural) | 0.1–1.0 mg | 0.5 mg |
| Lime (Natural) | 0.1–5.0 mg | 1.0 mg |
| Citric Acid | 1.0–10.0 mg | 5.0 g |

It is understood, however, that certain substitutions, deletions and additions of other ingredients would still provide the benefits of the present invention. Thus, all equivalents of the formula set forth above are intended to be encompassed by the scope of the claims.

While the L-arginine described above has been described as the free base, any suitable salt thereof is useful in the practice of the present invention.

The precise components of the formula set forth above are merely the preferred embodiments of the composition. Likewise, the weight value for each component is only the preferred value for the identified component.

In addition to L-arginine, three other amino acids are preferably present in the composition. Those amino acids include L-leucine, L-isoleucine and L-valine. All three of those amino acids are neutral aliphatic amino acids. Leucine has the formula $CH_3CH(CH_3)CH(NH_2)COOH$. Isoleucine has the formula $CH_3CH_2CH(CH_3)CH(NH_2)COOH$. Valine has the formula $CH_3CH(CH_3)CH(NH_2)COOH$.

Boron is an element of Group III-A of the Periodic Table. The more important minerals of boron are trimcal $[Na_2B_4O_7.10H_2O]$, boracite $[2Mg_3B_8O_{15}.MgCl_2]$, borocalcite or ulexite $[Na_2B_4O_7.2CaB_4O_7.18H_2O]$. Several oxyacids or salts thereof are known, the most prominent among which are orthoboric [$H_3BO_3$], (poly)metaboric [$(HB_2)_n$], tetraboric [$H_2B_4O_7$], and peroxyboric (perboric) [$HBO_3$]. Boron has been classified as an adaptagen.

Another component of the composition, calcium pantothenate, also known as vitamin B5, has the chemical formula

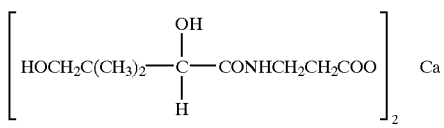

Chromium is an essential trace element usually found in foods. For biological activity, chromium should preferably be trivalent, i.e., chromium (III).

A wide margin of safety separates toxicity from the nutritional requirement of chromium (III).

Trans ferulic acid is the metabolically active form of gamma oryzanol. Gamma oryzanol is a mixture of ferulic acid esters of sterols(compestrol, stigmasterol, beta-sitostarol) and triterpene alcohols (cycloartanol, beta-sitostarol) and triterpene alcohols extracted from rice bran, corn and barley oils. Oryzanol A and Oryzanol C are two types.

Choline is known as (beta-hydroxyethyl) trimethylammonium hydroxide and has the chemical formula

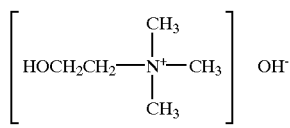

It is synthesized in the human body. Choline does not exist as a base in the body but rather as a salt using whatever anion is present in its immediate biological environment. Choline is believed to work with arginine to cause the hypothalamus to release growth hormone releasing factor to the pituitary.

Fructose has the structure

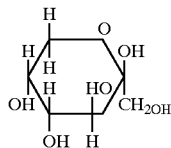

Fructose is a sugar, a type of carbohydrate, which is sweet to the taste and is highly soluble in water.

Fructose is identified in the preferred L-arginine composition of the present invention to provide a pleasant taste to the final product. Any other sugar may be substituted or added as long as the taste or flavor is flavorable.

Lemon and/or lime flavor may be included for their flavor enhancing properties. Those constituents, because of their acid properties, may also contribute to the control of the pH of the composition. Citric acid, identified above in connection with the pH control, also serves to impart favorable flavor and patient tolerance to the composition.

The preferred composition of the present invention as identified above is preferably in oral form as a capsule, powder, or similar dosage form. The composition may be made by simply mixing the ingredients together in the desired proportions and adding $H_2O$.

Preferably, the L-arginine is formulated with any suitable nontoxic inert carrier material. Such carrier materials are well known to those skilled in the art of pharmaceutical formulations. For those not skilled in the art, reference is made to the text entitled "Remington's Pharmaceutical Sciences."

In a typical preparation for oral administration, e.g., powder or capsule, the active ingredient, i.e., L-arginine, may be combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents may be included. Typical binders include starch, gelatin, sugars such as sucrose, molasses and lactose, natural and synthetic gums such as acacia, sodium alginate, extract or Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate.

If desired, a conventional acceptable dye can be incorporated into the dosage unit form, i.e., any of the standard FD&C dyes. Sweetening and flavoring agents and preservatives can also be included, particularly when a liquid dosage form is formulated, e.g., an elixir, suspension or syrup. Also, when the dosage form is capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both.

While not being bound to any theory, the mechanism of the action of the L-arginine in stimulating or enhancing muscle growth is understood as follows. L-Arginine stimulates (as a precursor) the hypothalamus to trigger the pituitary to release its own natural store of growth hormone; as such, it is not considered a drug. It is understood that the L-arginine acts as a growth hormone precursor to have a direct involvement on increasing muscle mass.

The L-arginine and preferred composition comprising L-arginine as identified above are useful in stimulating or enhancing muscle growth. Thus, the L-arginine or composition of L-arginine may be useful as an ergogenic aid. The inventor has discovered that the mammalian body, e.g., the human body, seems to respond by increasing its muscle mass and decreasing body fat when L-arginine is administered. The L-arginine and L-arginine formulations of the present invention are particularly suitable for athletes.

Each of the ingredients identified in the above formula has been approved by the FDA and are classified as a food or vitamin. The formulation complies with the guidelines as set forth by the Council for Responsible Nutrition.

While the present invention is described above in connection with preferred or illustrative embodiments, those embodiments are not intended to be exhaustive or limiting of the invention. Rather, the invention is intended to cover all alternatives, modifications and equivalents included within its spirit and scope.

EXAMPLE 1

A preferred composition of the invention was formulated as follows.

|  | Preferred Dosage |
| --- | --- |
| L-Arginine (free base) | 6.0 grams |
| L-Leucine | 100.0 Milligrams |
| L-Isoleucine | 50.0 Milligrams |
| L-Valine | 50.0 Milligrams |
| Boron (Sodium Borate) | 2.0 Milligrams |
| Vitamin B5 (Calcium Pantothenate) | 50.0 Milligrams |
| Chromium | 25.0 Micrograms |
| Trans Ferulic Acid | 10.0 to 15.0 Milligrams |
| Gamma Oryzanol | 15.0 Milligrams |
| Choline | 50.0 Milligrams |
| Fructose | 6.0 Grams |
| Lemon (Natural) | 0.5 Milligrams |
| Lime (Natural) | 1.0 Milligrams |
| Citric Acid | 5.0 Grams |

The above composition (identified as M2) was administered to test subjects. Those tests and the results are described in Example 2.

EXAMPLE 2

| (1) | Male Subject | Subject took M2 orally from 1984 to 1991 |
| --- | --- | --- |
|  | age 38 | Dose: 2–30 grams L-Arginine REM sleep + food ~ food |
|  | 20 lbs overweight |  |
|  | BP 120/80 |  |

Result: Subject lost 20 lbs bodyfat with an increase in muscle mass calculated to be 9 lbs. during the first 12 months from 1984. The subject did not change his diet or exercise program.

Immune system response: The subject no longer suffers from colds, flu.

Other: The subject reports substantially more energy, increased strength, tighter skin, gums no longer bleed during dental procedures.

Side-Effects: Subject has taken M2 for 8 years with no negative side-effects.

Therapeutic dose for this subject: 15 grams L-Arginine per day

Antagonists: Other proteins not in free form, high glycemic foods, lysine.

| (2) | Male Subject | Subject took M2 orally from 1984 to 1990 |
| --- | --- | --- |
|  | age 24 | Dose: 30–50 gms L-Arginine per day |
|  |  | Day + food = food REM = food |
|  | 187 lbs |  |
|  | BP normal |  |

Result: Subject took M2 with varying degrees of diarrhea which did not effect growth hormone response. Increases in dose resulted in decreased stool density. Reducing vitamin C and increasing citric acid had effect on tolerance of L-Arginine at higher doses.

Subject claims he is much stronger and feels more energetic.

At 6 months: Subject had gained 15 lbs of lean muscle and lost 3% bodyfat. The subject reported being hungrier, being able to exercise harder without feeling tired and having an increased feeling of well being and overall health.

At 1 year+: Subject has continued to experience muscle gain and strength gain and wishes to continue with the program.

2 +years: Muscle increase leveled off, but was retained, caloric requirements greatly increased probably due to increase in muscle mass.

Side-Effects: Other than diarrhea, no negative side-effects after 7 years. The subject was able to control effect of diarrhea by increasing ratios of citric acid to L-Arginine. Growth Hormone response out of pituitary gland requires, in this case, 15–20 grams L-Arginine on a totally empty stomach: 3 +hours.

(3) Female Subject

1983—Polychlorinated Byphenol Poisoning Diagnosed.

Cause: Exposure to PCB's while working on Environmental Protection Agency contract as part of scholarship in Environmental Chemistry. The subject breathed PCB's for two years in the laboratory while setting toxic guidelines for EPA. PCB's have been determined to be carcinogenic.

Result of exposure: Stomach and Esophageal cancer with metastasis to diaphragm and surrounding tissue, including deepest muscle biopsy. PCB cyst also found on liver and ovary.

Diagnosis: Terminal

Treatment: Surgery to remove as much cancer as possible, remove rib cage section, remove and resect stomach, remove distal esophagus, remove liver cyst, leave ovarian cyst.

Subject cannot receive chemotherapy or radiation due to nature of disease and new location of stomach (next to heart)

After experimental surgery, it was felt by attending physicians that no treatment could be given. It was reported that no one has ever survived this disease, and subject had remaining metastases.

The subject was placed on L-Arginine M2 therapy. No toxicity to vitamins noted, and was well tolerated by the subject. The subject continues to improve on this regimen.

While the invention has now been described with reference to several preferred embodiments, those skilled in the art will appreciate that various substitutions, omissions, modifications and changes may be made without departing from the scope or spirit thereof. Accordingly, it is intended that the foregoing description be considered merely exemplary of the invention and not a limitation thereof.

I claim:

1. A method for stimulating growth of muscle in a mammalian organism, said method comprising the step of administering to a mammalian organism in need of increased muscle growth a muscle growth stimulating effective amount of a composition consisting essentially of:

| L-arginine | 1.0–60.0 g |
| --- | --- |
| L-leucine | 25–200 mg |
| L-isoleucine | 25–200 mg |
| L-valine | 25–200 mg |
| boron | 1.0–30 mg |
| vitamin B5 | 10–100 mg |

-continued

|  |  |
|---|---|
| chromium | 10–50 micrograms |
| choline | 10.0–700 mg |
| fructose | 2.0–10.0 g | and citric acid in an amount of 1.0–10.0 mg for controlling the pH of the composition at less than 7.0, and an acceptable carrier therefore; and wherein said composition optionally has trans ferulic acid in an amount of 5.0 to 100 mg, gamma oryzanol in an amount of 5.0 to 100 mg, lemon flavor in an amount of 0.1–1.0 mg and lime flavor in an amount of 0.1–5.0 mg.

2. The method as claimed in claim 1, wherein the composition is administered orally.

3. The method as claimed in claim 2, wherein trans ferulic acid in an amount of 5.0 to 100 mg, gamma oryzanol in an amount of 5.0 to 100 mg, lemon flavor in an amount of 0.1–1.0 mg and lime flavor in an amount of 0.1–5.0 mg are present.

4. The method according to claim 2, wherein said L-arginine is present in an amount of 6.0 g, said L-leucine is present in an amount of 100.0 mg, said L-isoleucine is present in an amount of 50.0 mg, said L-valine is present in an amount of 50.0 mg, said boron is present in an amount of 2.0 mg, said vitamin B5 is present in an amount of 50 mg, said chromium is present in an amount of 25.0 mcg, said choline is present in an amount of 50.0 mg, and said fructose is present in an amount of 6.0 g.

5. A method for stimulating an immune response in a mammalian organism, said method comprising the step of administering to a mammal in need thereof an effective amount of a composition consisting essentially of:

|  |  |
|---|---|
| L-arginine | 1.0–60.0 g |
| L-leucine | 25–200 mg |
| L-isoleucine | 25–200 mg |
| L-valine | 25–200 mg |
| boron | 1.0–30 mg |
| vitamin B5 | 10–100 mg |
| chromium | 10–50 micrograms |
| choline | 10.0–700 mg |
| fructose | 2.0–10.0 g | and citric acid in an amount of 1.0–10.0 mg for controlling the pH of the composition at less than 7.0, and an acceptable carrier therefor.

6. The method according to claim 5, wherein said composition is administered intravenously as an aqueous solution in an amount of 1–10 g per day.

7. The method according to claim 6, wherein said composition is administered in association with an immune system stimulator.

8. The method according to claim 7, wherein said immune system stimulator is vitamin C and is administered in an amount of about 1–10 g per day.

9. A composition for stimulating muscle growth, said composition consisting essentially of:

|  |  |
|---|---|
| L-arginine | 1.0–60.0 g |
| L-leucine | 25–200 mg |
| L-isoleucine | 25–200 mg |
| L-valine | 25–200 mg |
| boron | 1.0–30 mg |
| vitamin B5 | 10–100 mg |
| chromium | 10–50 micrograms |
| choline | 10.0–700 mg |
| fructose | 2.0–10.0 g | and citric acid in an amount of 1.0–10.0 mg for controlling the pH of the composition at less than 7.0, and an acceptable carrier therefor; and wherein said composition optionally has trans ferulic acid in an amount of 5.0 to 100 mg, gamma oryzanol in an amount of 5.0 to 100 mg, lemon flavor in an amount of 0.1–1.0 mg and lime flavor in an amount of 0.1–5.0 mg.

10. The composition as claimed in claim 9, wherein said citric acid controls the pH at less than 6.0.

11. The composition according to claim 10, wherein the citric acid controls the pH at about 4.5 to 4.7.

12. The composition according to claim 9, wherein the weight ratio of citric acid: L-arginine is 0.001–1:1.

13. The composition according to claim 12, wherein the weight ratio is 0.01–0.9:1.

14. The composition according to claim 9, wherein trans ferulic acid in an amount of 5.0–100 mg, gamma oryzanol in an amount of 5.0–100 mg, lemon flavor in an amount of 0.1–1.0 mg and lime flavor in an amount of 0.1–5.0 mg are present.

15. A composition for stimulating muscle growth, said composition consisting essentially of:

|  |  |
|---|---|
| L-arginine (free base) | 60.0 g |
| L-leucine | 100.0 mg |
| L-isoleucine | 50.0 mg |
| L-valine | 50.0 mg |
| sodium borate | 2.0 mg |
| vitamin B5 | 50.0 mg |
| chromium | 25.00 mg |
| trans ferulic acid | 10.0 mg |
| gamma oryzanol | 15.0 mg |
| choline | 50.0 mg |
| fructose | 6.0 grams |
| lemon | 0.5 mg |
| lime | 1.0 mg | and citric acid in an amount of 5.0 mg for controlling the pH of die composition at less than 7.0, and an acceptable carrier therefor.

* * * * *

UNITED STATES PATENT AND TRADEMARK OFFICE
CERTIFICATE OF CORRECTION

PATENT NO. : 6,608,109 B2  Page 1 of 1
DATED : August 19, 2003
INVENTOR(S) : Ann de Wees Allen It is certified that error appears in the above-identified patent and that said Letters Patent is hereby corrected as shown below:

<u>Title page, Item [54] and Column 1, line 1,</u>
Title, "COMPOSITION COMPRISING" should read -- A COMPOSITION COMPRISING --.

<u>Column 2,</u>
Line 7, "As a result, long term therapy. with" should read -- As a result, long term therapy with --.
Line 10, "consequential reduced.incidence" should read -- consequential reduced incidence --.

<u>Column 4,</u>
Line 35, "Chromium, "10-50 micrograms" should read -- 10-50 mg --.
Line 35, "Chromium, "25.0 micrograms" should read -- 25.0 mg --.
Line 36, "Trans Ferulic Acid, "10 0 mg" should read -- 10.0 mg --.

<u>Column 5,</u>
Line 5, "known as vitamin BS" should read -- known as vitamin B5 --.

<u>Column 7,</u>
Line 15, "Chromium, "25.0 Micrograms" should read -- 25.0 Milligrams --.

<u>Column 10,</u>
Line 55, "of die composition" should read -- of the composition --.

Signed and Sealed this

Sixteenth Day of December, 2003

JAMES E. ROGAN
*Director of the United States Patent and Trademark Office*